United States Patent
Gil-Lopetegui et al.

[11] Patent Number: 6,057,441
[45] Date of Patent: May 2, 2000

[54] SUBSTITUTED TETRACYCLIC TETRAHYDROFURAN DERIVATIVES

[75] Inventors: Pilar Gil-Lopetegui; Francisco Javier Fernández-Gadea, both of Toledo, Spain; Theo Frans Meert, Boom, Belgium

[73] Assignee: Janssen Pharmaceutica, N.V., Beerse, Belgium

[21] Appl. No.: 09/155,840

[22] PCT Filed: Apr. 9, 1997

[86] PCT No.: PCT/EP97/01829

§ 371 Date: Oct. 6, 1998

§ 102(e) Date: Oct. 6, 1998

[87] PCT Pub. No.: WO97/38991

PCT Pub. Date: Oct. 23, 1997

[30] Foreign Application Priority Data

Apr. 12, 1996 [EP] European Pat. Off. .............. 96200990

[51] Int. Cl.$^7$ ...................... C07D 223/14; C07D 337/12; C07D 313/00; C07D 211/08; C07D 405/00

[52] U.S. Cl. .......................... 540/576; 540/587; 544/359; 544/375; 544/380; 546/192; 546/195; 546/197; 546/202; 548/517; 548/454; 548/525; 548/526; 548/527; 548/528; 548/529; 549/12; 549/354

[58] Field of Search ...................... 540/587, 576; 549/12, 354; 544/359, 375, 380; 546/192, 195, 197, 202; 548/517, 525, 526, 527, 528, 529, 454

[56] References Cited

U.S. PATENT DOCUMENTS

| | | |
|---|---|---|
| 5,089,507 | 2/1992 | Vecchietti et al. . |
| 5,286,735 | 2/1994 | Bonnaud et al. . |
| 5,310,743 | 5/1994 | Schilling et al. . |
| 5,541,195 | 7/1996 | Schilling et al. . |
| 5,646,144 | 7/1997 | Schilling et al. . |

FOREIGN PATENT DOCUMENTS

| | | |
|---|---|---|
| 0 532 398 | 3/1993 | European Pat. Off. . |
| WO 97/10212 | 3/1997 | WIPO . |

OTHER PUBLICATIONS

Goodman & Gilman's, *The Pharmacological Basis of Therapeutics*, ninth edition, McGraw–Hill, New York, Chapter 7:148–160 (1996).

*Primary Examiner*—John Kight
*Assistant Examiner*—Raymond Covington
*Attorney, Agent, or Firm*—Mary A. Appollina

[57] ABSTRACT

This invention concerns the compounds of formula (I),

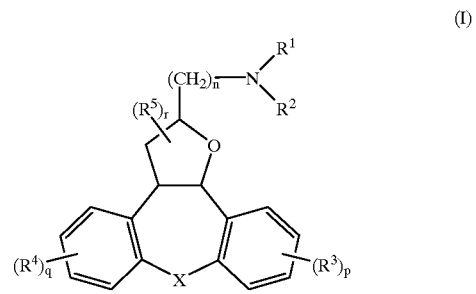

the N-oxide forms, the pharmaceutically acceptable addition salts and the stereoisomeric forms thereof, wherein n is zero to 6; p and q are zero to 4; r is zero to 5; $R^1$ and $R^2$ each independently are hydrogen; optionally substituted $C_{1-6}$alkyl; $C_{1-6}$alkylcarbonyl; halomethylcarbonyl; or $R^1$ and $R^2$ taken together with the nitrogen atom to which they are attached may form a morpholinyl ring or an optionally substituted heterocycle; each $R^3$ and $R^4$ independently are halo, cyano, hydroxy, halomethyl, halomethoxy, carboxyl, nitro, amino, mono- or di($C_{1-6}$alkyl)amino, $C_{1-6}$alkylcarbonylamino, aminosulfonyl, mono- or di($C_{1-6}$alkyl)aminosulfonyl, $C_{1-6}$alkyl, $C_{1-6}$alkyloxy, $C_{1-6}$alkylcarbonyl, $C_{1-6}$alkyloxycarbonyl; each $R^5$ independently is $C_{1-6}$alkyl, cyano or halomethyl; X is $CR^6R^7$, $NR^8$, O, S, S(=O) or S(=O)$_2$; aryl is optionally substituted phenyl; provided that the compound is other than (±)-3,3a, 8,12b-tetrahydro-N-methyl-2H-dibenzo[3,4:6,7]-cyclohepta[1,2-b]-furan-2-methanamine oxalic acid. The compounds of formula (I) may be used as therapeutic agents in the treatment or the prevention of CNS disorders, cardiovascular disorders or gastrointestinal disorders.

12 Claims, No Drawings

SUBSTITUTED TETRACYCLIC TETRAHYDROFURAN DERIVATIVES

CROSS REFERENCE TO RELATED APPLICATIONS

This application is a National Stage application under 35 U.S.C. § 317 of PCT/EP97/01829 filed Apr. 9, 1997, which claims priority from EP 96.200.990.8, filed Apr. 12, 1996.

This invention concerns substituted tetracylic tetrahydrofuran derivatives having antipsychotic, cardiovascular and gastrokinetic activity and their preparations; it further relates to compositions comprising them, as well as their use as a medicine.

An article by Monkovic et al. (J. Med. Chem. (1973), 16(4), p. 403–407) describes the synthesis of (±)-3,3a,8,12b-tetrahydro-N-methyl-2H-dibenzo[3,4:6,7]-cyclohepta[1,2-b]furan-2-methanamine oxalic acid. Said compound was synthesized as potential antidepressant; however, it was found that this particular tetrahydrofurfurylamine derivative was inactive as antidepressant at a dose of 300 mg/kg. Compounds of similar structure are disclosed in U.S. Pat. No. 4,145,434, published on Mar. 20, 1979, and involve dibenzo(cyclohepta-, oxepino-, thiepino-) pyrrolidine derivatives as well as dibenzopyrrolidino azepine derivatives, having CNS-depressant, antihistamine and anti-serotonin activities. The present compounds differ therefrom structurally by the presence of a tetrahydrofuran ring instead of a pyrrolidine ring, and are further distinguished by valuable pharmacological properties, in particular, they suppress mCPP (metachlorophenylpiperazine) induced effects in rats.

This invention concerns compounds of formula (I)

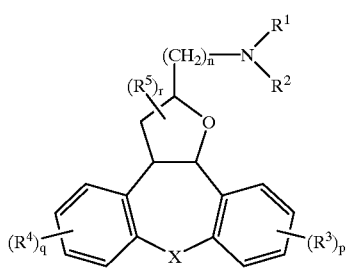

(I)

the N-oxide forms, the pharmaceutically acceptable addition salts and the stereochemically isomeric forms thereof, wherein:

n is zero, 1, 2, 3, 4, 5, or 6;
p is zero, 1, 2, 3 or 4;
q is zero, 1, 2, 3 or 4;
r is zero, 1, 2, 3, 4 or 5;
$R^1$ and $R^2$ each independently are hydrogen; $C_{1-6}$alkyl; $C_{1-6}$alkylcarbonyl;halomethylcarbonyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl; or $R^1$ and $R^2$ taken together with the nitrogen atom to which they are attached may form a morpholinyl ring or a radical of formula:

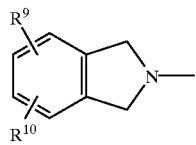

(a)

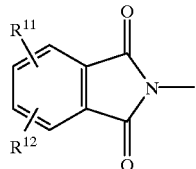

(b)

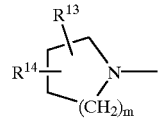

(c)

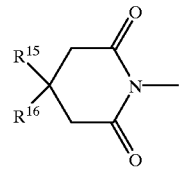

(d)

(e)

wherein:
$R^9$, $R^{10}$, $R^{11}$ and $R^{12}$ each independently are hydrogen, halo, halomethyl, or $C_{1-6}$alkyl;
m is zero, 1, 2, or 3;
$R^{13}$, $R^{14}$, $R^{15}$ and $R^{16}$ each independently are hydrogen, $C_{1-6}$alkyl, aryl or arylcarbonyl; or
$R^{15}$ and $R^{16}$ taken together may form a bivalent radical $C_{4-5}$alkanediyl;
$R^{17}$ is hydrogen; $C_{1-6}$alkyl; $C_{1-6}$alkylcarbonyl; halomethylcarbonyl;
$C_{1-6}$alkyloxycarbonyl; aryl; di(aryl)methyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl;
each independently is halo, cyano, hydroxy, halomethyl, halomethoxy, carboxyl, nitro, amino, mono- or di($C_{1-6}$alkyl)amino, $C_{1-6}$alkylcarbonylamino, aminosulfonyl, mono- or di($C_{1-6}$alkyl)aminosulfonyl, $C_{1-6}$alkyl, $C_{1-6}$alkyloxy, $C_{1-6}$alkylcarbonyl, $C_{1-6}$alkyloxycarbonyl;
each $R^4$ independently is halo, cyano, hydroxy, halomethyl, halomethoxy, carboxyl, nitro, amino, mono- or di($C_{1-6}$alkyl)amino, $C_{1-6}$alkylcarbonylamino, aminosulfonyl, mono- or di($C_{1-6}$alkyl)aminosulfonyl, $C_{1-6}$alkyl, $C_{1-6}$alkyloxy, $C_{1-6}$alkylcarbonyl, $C_{1-6}$alkyloxycarbonyl;
each $R^5$ independently is $C_{1-6}$alkyl, cyano or halomethyl;
X is $CR^6R^7$, $NR^8$, O, S, S(=O) or S(=O)$_2$; wherein
$R^6$ and $R^7$ each independently are hydrogen, hydroxy, $C_{1-6}$alkyl, halomethyl, $C_{1-6}$alkyloxy or $R^6$ or $R^7$ taken together may form methylene; mono- or di(cyano)methylene; a bivalent radical of formula —($CH_2$)$_2$—, —($CH_2$)$_3$—, —($CH_2$)$_4$—, —($CH_2$)$_5$—, —O—(CH$_2$)$_2$—O—, —O—(CH$_2$)$_3$—O—; or, together with the carbon atom to which they are attached, a carbonyl;

R$^8$ is hydrogen, C$_{1-6}$alkyl, C$_{1-6}$alkylcarbonyl, arylcarbonyl, arylC$_{1-6}$alkylcarbonyl, C$_{1-6}$alkylsulfonyl, arylsulfonyl or arylC$_{1-6}$alkylsulfonyl;

aryl is phenyl; or phenyl substituted with 1, 2 or 3 substituents selected from halo, hydroxy, C$_{1-6}$alkyl and halomethyl; provided that the compound is other than (±)-3,3a,8,12b-tetrahydro-N-methyl-2H-dibenzo[3,4:6,7]-cyclohepta[1,2-b]furan-2-methanamine oxalic acid.

In the foregoing definitions C$_{1-6}$alkyl defines straight and branch chained saturated hydrocarbon radicals having from 1 to 6 carbon atoms such as, for example, methyl, ethyl, propyl, butyl, 1-methylpropyl, 1,1-dimethylethyl, pentyl, hexyl; C$_{4-5}$alkanediyl defines bivalent straight and branch chained saturated hydrocarbon radicals having from 4 to 5 carbon atoms such as, for example, 1,4-butanediyl, 1,5-pentanediyl; halo is generic to fluoro, chloro, bromo and iodo. The term monocyanomethylene stands for a radical of formula =CHCN, and dicyanomethylene for a radical of formula =C(CN)$_2$. The term halomethyl is meant to include mono, di-, and trihalomethyl. Examples of halomethyl are fluoromethyl, difluoromethyl and particularly trifluoromethyl. In case R$^6$ and R$^7$ taken together form a bivalent radical of formula —(CH$_2$)$_2$—, —(CH$_2$)$_3$—, —(CH$_2$)$_4$—, —(CH$_2$)$_5$—, —O—(CH$_2$)$_2$—O or —O—(CH$_2$)$_3$—O—, the compounds of formula (I) are spiro compounds.

The pharmaceutically acceptable addition salts as mentioned hereinabove are meant to comprise the therapeutically active non-toxic base and acid addition salt forms which the compounds of formula (I) are able to form. The acid addition salt form of a compound of formula (I) that occurs in its free form as a base can be obtained by treating the free base form of the compound of formula (I) with an appropriate acid such as an inorganic acid, for example, hydrohalic acid, e.g. hydrochloric or hydrobromic, sulfuric, nitric, phosphoric and the like acids; or an organic acid, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicyclic, p-aminosalicylic, pamoic and the like acids.

The compounds of formula (I) containing acidic protons may be converted into their therapeutically active non-toxic base, i.e. metal or amine, addition salts forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Conversely said salt forms can be converted into the free forms by treatment with an appropriate base or acid.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I) are meant to comprise those compounds of formula (I) wherein one or several nitrogen atoms are oxidized to the so-called N-oxide, particularly those N-oxides wherein the nitrogen bearing the R$^1$ and R$^2$ substituents is N-oxidized.

The term "stereochemically isomeric forms" as used hereinbefore and hereinafter defines all the possible isomeric forms in which the compounds of formula (I) may occur. Unless otherwise mentioned or indicated, the chemical designation of compounds denotes the mixture, and in particular the racemic mixture, of all possible stereochemically isomeric forms, said mixtures containing all diastereomers and enantiomers of the basic molecular structure. Stereochemically isomeric forms of the compounds of formula (I) and mixtures of such forms are intended to be encompassed by formula (I).

The numbering of the tetracyclic ring-system present in the compounds of formula (I), as defined by Chemical Abstracts nomenclature is shown in formula (I').

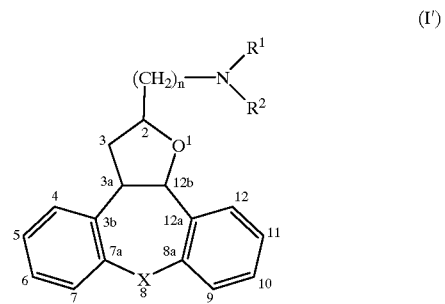

(I')

The compounds of formula (I) have at least three asymmetric centers, namely carbon atom 2, carbon atom 3a and carbon atom 12b. Said asymmetric centers and any other asymmetric center which may be present, are indicated by the descriptors R and S.

When a monocyanomethylene moiety is present in the compounds of formula (I), said moiety may have the E- or Z-configuration.

The substituents on carbon atoms 3a and 12b, i.e. hydrogen or R$^5$, may have a cis or trans configuration. In determining said cis or trans configuration, carbon atoms 3b and 12a are not considered as relevant substituents as they both are part of the same ring system. When establishing the configuration of carbon atoms 3a and 12b, the substituent on carbon atom 3a and the substituent on carbon atom 12a are considered. They may be on the same side of the mean plane determined by the tetrahydrofuranyl ring, then the configuration is designated cis, if not, the configuration is designated trans. Preferably, the substituents on carbon atoms 3a and 12b are both hydrogen and are each on a different side of the mean plane determined by the tetrahydrofuranyl ring, i.e. they have the trans configuration.

Whenever used hereinafter, the term "compounds of formula (I)" is meant to also include the pharmaceutically acceptable addition salts, the stereoisomeric forms, and also the N-oxide forms.

A particular group of compounds comprises those compounds of formula (I) wherein R$^{13}$, R$^{14}$, R$^{15}$ and R$^{16}$ each independently are hydrogen or C$_{1-6}$alkyl.

Of particular interest are those compounds of formula (I) that are other than 3,3a, 8,12b-tetrahydro-N-methyl-2H-dibenzo[3,4:6,7]-cyclohepta[1,2-b]furan-2-methanamine.

Interesting compounds are those compounds of formula (I) wherein R$^1$ and R$^2$ are both C$_{1-6}$alkyl.

Other interesting compounds are those compounds of formula (I) wherein R$^1$ and R$^2$ are taken together with the nitrogen atom to which they are attached and form a morpholinyl ring; a radical of formula (c), in particular, a radical of formula (c) wherein m is 2, R$^{13}$ is hydrogen and R$^{14}$ is aryl or arylcarbonyl; or a radical of formula (e), in particular a radical of formula (e) wherein R$^{17}$ is aryl, C$_{1-4}$alkyl or hydroxyC$_{1-4}$alkyl.

Still other interesting compounds are those compounds of formula (I) wherein X is CR$^6$R$^7$ or O.

Particular compounds are those compounds of formula (I) wherein R$^1$ and R$^2$ are both methyl and n is 1.

Further particular compounds are those compounds of formula (I) wherein p is 1 and R$^3$ is halo, C$_{1-6}$alkyl or C$_{1-6}$alkyloxy, in particular halo.

Other particular compounds are those compounds of formula (I) wherein q is 1 and R$^4$ is halo, C$_{1-6}$alkyl or C$_{1-6}$alkyloxy, in particular halo.

Still other particular compounds are those compounds of formula (I) wherein p, q and r are zero.

Preferred compounds are those particular compounds wherein r is zero and the hydrogen atoms on carbon atoms 3a and 12b have a trans configuration.

Most preferred are 3,3a,8,12b-tetrahydro-N,N-dimethyl-2H-dibenzo[3,4:6,7]cyclohepta[1,2-b]furan-2-methanamine; the stereochemically isomeric forms and the pharmaceutically acceptable addition salts thereof, and the N-oxide forms thereof, more in particular, those isomeric forms wherein the hydrogen atoms on carbon atoms 3a and 12b have a trans configuration.

The compounds of formula (I) can generally be prepared by N-alkylating an intermediate of formula (II) with an intermediate of formula (III) wherein W is a suitable leaving group such as halo. In the intermediates (II) and (III), R$^1$ to R$^5$, n, p, q, r and X are as defined in the compounds of formula (I). Said N-alkylation can conveniently be carried out in a reaction-inert solvent such as, for example, methanol, methylisobutyl ketone, N,N-dimethylformamide or dimethylsulfoxide, and optionally in the presence of a suitable base. Stirring and elevated temperatures, for instance reflux temperature, may enhance the rate of the reaction. Alternatively, said N-alkylation may also be performed using the procedure described by Monkovic et al. (J. Med. Chem. (1973), 16(4), p. 403–407) which involves the use of a pressurized reaction vessel.

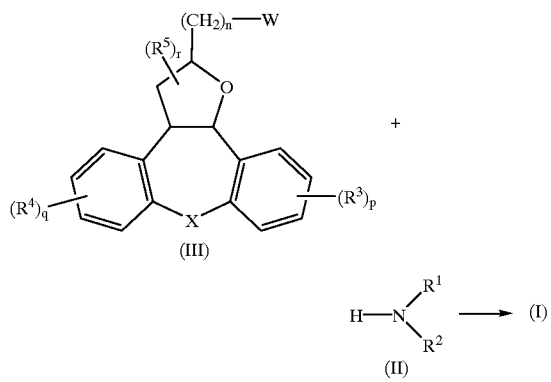

The compounds of formula (I) may also be converted into each other following art-known transformation reactions. For instance, a) a compound of formula (I), wherein R$^1$ and R$^2$ taken together with the nitrogen atom to which they are attached form a radical of formula (b), may be converted into the corresponding primary amine by treatment with hydrazine or aqueous alkali;

b) a compound of formula (I), wherein R$^1$ or R$^2$ is trifluoromethylcarbonyl, may be converted into the corresponding primary or secondary amine by hydrolysis with aqueous alkali;

c) a compound of formula (I), wherein R$^1$ or R$^2$ is C$_{1-6}$alkyl substituted with C$_{1-6}$alkylcarbonyloxy may be hydrolyzed into a compound of formula (I) wherein R$^1$ or R$^2$ is C$_{1-6}$alkyl substituted with hydroxy;

d) a compound of formula (I), wherein R$^1$ and R$^2$ are both hydrogen may be mono- or di-N-alkylated to the corresponding amine form;

e) a compound of formula (I), wherein R$^1$ and R$^2$ are both hydrogen may be N-acylated to the corresponding amide;

f) a compound of formula (I), containing a C$_{1-6}$alkyloxycarbonyl group may be hydrolyzed to the corresponding carboxylic acid.

In addition, the compounds of formula (I) wherein X is other than S may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid respectively with a suitable chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The intermediates mentioned hereinabove are either commercially available or may be made following art-known procedures. For instance, intermediates of formula (III) may be prepared according to the procedure described by Monkovic et al. (J. Med. Chem. (1973), 16(4), p. 403–407).

Alternatively, intermediates of formula (III) wherein n is 1 and r is 0, said intermediates being represented by formula (III-a), can also be prepared by reacting an epoxide derivative of formula (IV) with a Grignard reagent of formula (V) wherein X suitably is halo, thus forming an intermediate of formula (VI) which may subsequently be cyclized according to art-known methods such as the one described in Monkovic et al.

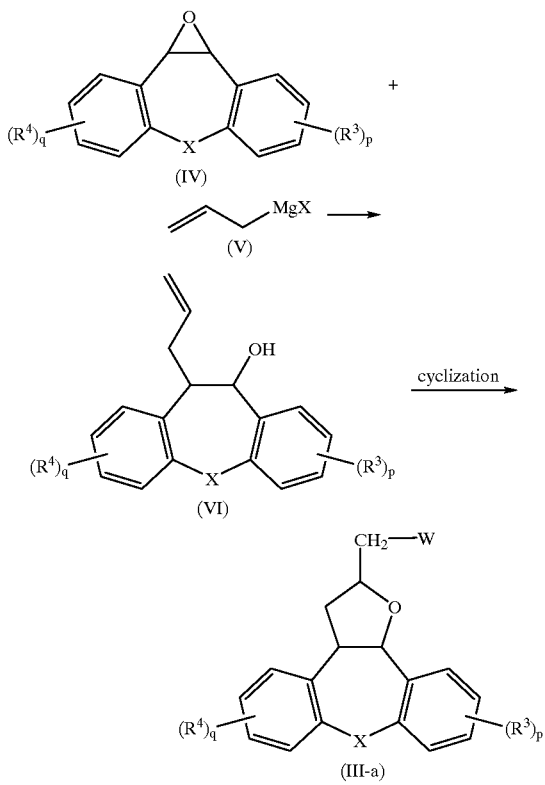

Epoxides of formula (IV) can be prepared using art-known procedures such as peroxidating an intermediate of formula (VII) with a suitable peroxide such as m-chloroperbenzoic acid.

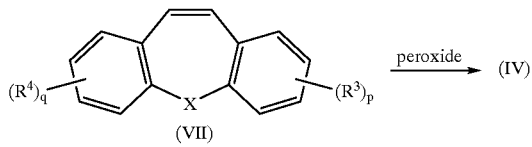

The compounds of the present invention show affinity for 5-HT$_2$ receptors, particularly for 5-HT$_{2A}$ and 5-HT$_{2C}$ receptors (nomenclature as described by D. Hover in "Serotonin (5-HT) in neurologic and psychiatric disorders" edited by M. D. Ferrari and published in 1994 by the Boerhaave Commission of the University of Leiden). The serotonin antagonistic properties of the present compounds may be demonstrated by their inhibitory effect in the "5-hydroxytryptophan Test on Rats" which is described in Drug Dev. Res., 13, 237–244 (1988). Furthermore, the compounds of the present invention show interesting pharmacological activity in the "mCPP Test on Rats" which is described hereinafter, and in the "Combined Apomorphine, Tryptamine, Norepinephrine (ATN) Test on Rats" which is described in Arch. Int. Pharmacodyn, 227, 238–253 (1977).

The compounds of the present invention have favourable physicochemical properties. For instance, they are chemically stable compounds.

In view of these pharmacological and physicochemical properties, the compounds of formula (I) are useful as therapeutic agents in the treatment or the prevention of central nervous system disorders like anxiety, depression and mild depression, bipolar disorders, sleep- and sexual disorders, psychosis, borderline psychosis, schizophrenia, migraine, personality disorders or obsessive-compulsive disorders, social phobias or panic attacks, organic mental disorders, mental disorders in children, aggression, memory disorders and attitude disorders in older people, addiction, obesity, bulimia and similar disorders. In particular, the present compounds may be used as anxiolytics, antipsychotics, antidepressants, anti-migraine agents and as agents having the potential to overrule the addictive properties of drugs of abuse.

The compounds of formula (I) may also be used as therapeutic agents in the treatment of motoric disorders. It may be advantageous to use the present compounds in combination with classical therapeutic agents for such disorders.

The compounds of formula (I) may also serve in the treatment or the prevention of damage to the nervous system caused by trauma, stroke, neurodegenerative illnesses and the like; cardiovascular disorders like high blood pressure, thrombosis, stroke, and the like; and gastrointestinal disorders like dysfunction of the motility of the gastrointestinal system and the like.

In view of the above uses of the compounds of formula (I), it follows that the present invention also provides a method of treating warm-blooded animals suffering from such diseases, said method comprising the systemic administration of a therapeutic amount of a compound of formula (I) effective in treating the above-described disorders, in particular, in treating anxiety, psychosis, depression, migraine and addictive properties of drugs of abuse.

The present invention thus also relates to compounds of formula (I) as defined hereinabove for use as a medicine, in particular, the compounds of formula (I) may be used for the manufacture of a medicament for treating anxiety, psychosis, depression, migraine and addictive properties of drugs of abuse.

Those of skill in the treatment of such diseases could determine the effective therapeutic daily amount from the test results presented hereinafter. An effective therapeutic daily amount would be from about 0.01 mg/kg to about 10 ms/kg body weight, more preferably from about 0.05 mg/kg to about 1 mg/kg body weight.

For ease of administration, the subject compounds may be formulated into various pharmaceutical forms for administration purposes. To prepare the pharmaceutical compositions of this invention, a therapeutically effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid or base addition salts of compounds of formula (I) due to their increased water solubility over the corresponding base or acid form, are more suitable in the preparation of aqueous compositions.

In order to enhance the solubility and/or the stability of the compounds of formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds of formula (I) in pharmaceutical compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate and not to limit the scope of the present invention.

Experimental Part

A. Preparation of the Intermediate Compounds

EXAMPLE A.1 a) 3-Bromopropene (0.054 mol) was added dropwise to a mixture of dibenz[bf]oxepin-10(11H)-one (0.054 mol), prepared according to the procedure described in C.R. Acad. Sc. Paris, Serie C 1986, 283(15), 683–6, and potassium tert-butoxide (0.054 mol) in tert-butanol (100 ml), stirred at room temperature under a $N_2$ flow. The resulting reaction mixture was stirred for 2 hours at 80° C., then cooled to room temperature. The solvent was evaporated. The residue was partitioned between water and ethylacetate. The organic layer was separated, dried, filtered and the solvent was evaporated. The residue was purified by HPLC over a LiChroprep column (eluent: hexane/ethylacetate 98/2). The pure fractions were collected and the solvent was evaporated, yielding 4.5 g (32%) of (±)-11-(2-propenyl)dibenz[bf]oxepin-10(11H)-one (interm. 1).

b) Intermediate 1 (0.007 mol) and sodium borohydride (0.0033 mol) were dissolved in ethanol (40 ml). The reaction solution was stirred for 4 hours at 60° C., then cooled to room temperature. The reaction mixture was concentrated, then cooled in an ice-water bath. The reaction was quenched with water and this mixture was extracted with ethylacetate. The separated organic layer was dried, filtered, and the solvent was evaporated. The residue was purified by HPLC over a LiChroprep column (eluent: hexane/ethylacetate 90/10). The pure fractions were collected and the solvent was evaporated, yielding 0.85 g (50%) (±)-10,11-dihydro-11-(2-propenyl)dibenz[bf]oxepin-10-ol (interm. 2).

c) Intermediate 2 (0.0047 mol) and pyridine (0.0047 mol) were dissolved in carbon tetrachloride (40 ml) and the solution was cooled to 0° C. Bromine (0.0047 mol) was added and the resulting reaction mixture was stirred for 2 hours at room temperature. The mixture was washed with water. The organic layer was dried, filtered, and the solvent was evaporated. The residue was solidified by washing with diisopropylether, then dried, yielding 0.4 g (25%) of (±)-2-(bromomethyl)-2,3,3a,12b-tetrahydrodibenzo[bf]furo[2,3-d]oxepin (interm. 3).

EXAMPLE A.2 a) 1a,10b-dihydro-6H-dibenzo[3,4:6,7]cyclohept[1,2-b]oxirene (1 g) was dissolved in 15 ml tetrahydrofuran and cooled to 0° C., under $N_2$ atmosphere. Bromo-2-propenylmagnesium (5,2 ml, 1M in tetrahydrofuran) was added dropwise to the mixture and the mixture was stirred at room temperature and then at 60° C. for two hours. The mixture was cooled to room temperature and quenched with 10% $NH_4Cl$ and water, dried and the solvent was evaporated, yielding 0.5 g (48%) of 10,11-dihydro-11-(2-propenyl)-5H-dibenzo[a,d]cyclohepten-10-ol (interm. 4).

b) Pyridinium tribromide (0.63 g) was added portionwise to a solution of intermediate 4 (0.5 g) in $CHCl_3$ (15 ml). The mixture was stirred for one hour at −10° C. and then allowed to warm to room temperature. The mixture was stirred for another hour and was then washed with water, extracted, dried and the solvent was evaporated, yielding 0.42 g (65%) of (±)-2-(bromomethyl)-3,3a,8,12b-tetrahydro-2H-dibenzo[3,4:6,7]cyclohepta[1,2-b]furan (interm. 5).

B. Preparation of the Compounds of Formula (I)

The compounds prepared hereinafter all are mixtures of isomeric forms in which the substituents on carbon atoms 3a and 12b have the trans configuration, unless otherwise specified.

EXAMPLE B.1

A mixture of intermediate 3 (0.0012 mol) in dimethyl sulfoxide (60 ml) and chloroform (30 ml) was stirred and cooled to ±0° C. Dimethylamine (gas) was allowed to bubble through the mixture for 15 minutes. The reaction mixture was stirred for 24 hours at 65° C. in a Parr Pressure vessel. The reaction mixture was cooled to room temperature and concentrated, washed with water, and extracted with diethyl ether. The separated organic layer was dried, filtered and the solvent was evaporated. The residue was purified by HPLC over a LiChropren column (eluent: $CH_2Cl_2/CH_3OH$ 95/5). The pure fractions were collected and the solvent was evaporated, yielding 0.14 g (39%) of (±)-2,3,3a,12b-tetrahydro-N,N-dimethyldibenzo[bf]furo[2,3-d]oxepin-2-methanamine (comp. 1).

EXAMPLE B.2

A mixture of intermediate 5 (0.0045 mol) and 1-(2-hydroxyethyl)piperazine (0.0090 mol) was stirred for 2 hours at 120° C. The mixture was cooled to room temperature, then taken up into $CH_2Cl_2$, filtered and the filtrate was evaporated. The residue was purified by HPLC over LiChroprep (eluent: $CH_2Cl_2$/($CH_3OH$, saturated with $NH_3$) 96/4). The desired fractions were collected and the solvent was evaporated. The residue was converted into the hydrochloric acid salt (1:2). The precipitate was filtered off and dried, yielding 0.73 g (37%) of (±)-4-[(3,3a,8,12b-tetrahydro-2H-dibenzo[3,4:6,7]cyclohepta[1,2-b]furan-2-yl)methyl]-1-piperazineethanol dihydrochloride (comp. 3).

EXAMPLE B.3 a) A mixture of intermediate 5 (0.030 mol) and dimethylamine (2 M in tetrahydrofuran; 150 ml) was diluted with tetrahydrofuran (100 ml) and stirred overnight at 65° C. in a Parr pressure vessel. The reaction mixture was cooled to room temperature, and filtered. The filtrate was evaporated. The residue was purified by HPLC over LiChroprep (eluent: $CH_2Cl_2$/($CH_3OH$/$NH_3$ (g)) 98/2). The pure fractions were collected and the solvent was evaporated. The residue was converted into the hydrochloric acid salt (1:1). The precipitate was filtered off and dried, yielding 0.8 g (8%) of (±)-3,3a,8,12b-tetrahydro-N,N-dimethyl-2H-dibenzo[3,4:6,7]cyclohepta[1,2-b]furan-2-methanamine hydrochloride (1:1) (comp. 4; melting point 237° C.). Four pure enantiomers resulted from the separation of compound 4, i.e. the [2R(2α,3aα,12bβ)]. [2R(2α,3aβ,12bα)], [2S(2α,3aα,12bβ)] and [2S(2α,3aβ,12bα)] isomeric forms.

Table 1 lists compounds of formula (I) which were prepared according to one of the above examples.

TABLE 1

| Co. No. | Ex. No. | X | R | Physical data |
|---|---|---|---|---|
| 1 | B. 1 | $CH_2$ | —$N(CH_3)_2$ | (±) |
| 2 | B. 1 | O | —$N(CH_3)_2$ | (±) |
| 3 | B. 2 | $CH_2$ |  | (±); HCl (1:1); m.p. 258° C. |
| 4 | B. 3 | $CH_2$ | —$N(CH_3)_2$ | (±); HCl (1:1); m.p. 237° C. |
| 4a | B. 3 | $CH_2$ | —$N(CH_3)_2$ | [2R(2α, 3aα, 12bβ)] |
| 4b | B. 3 | $CH_2$ | —$N(CH_3)_2$ | [2R(2α, 3aβ, 12bα)] |
| 4c | B. 3 | $CH_2$ | —$N(CH_3)_2$ | [2S(2α, 3aα, 12bβ)] |
| 4d | B. 3 | $CH_2$ | —$N(CH_3)_2$ | [2S(2α, 3aβ, 12bα)] |
| 5 | B. 2 | $CH_2$ |  | (±); m.p. 276° C.; $H_2O$ (1:2).HCl (1:1) |
| 6 | B. 2 | $CH_2$ |  | (±); HCl (1:1) |
| 7 | B. 2 | $CH_2$ |  | (±); m.p. 208° C.; HBr (1:1) |

TABLE 1-continued

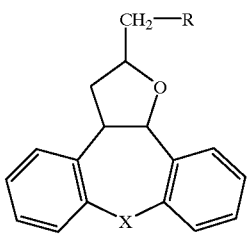

CH₂—R structure with X bridging two benzene rings

| Co. No. | Ex. No. | X | R | Physical data |
|---|---|---|---|---|
| 8 | B. 2 | CH₂ | (piperidinyl-C(=O)-C₆H₄-F) | (±); m.p. 253° C.; H₂O (1:1).HCl (1:1) |
| 9 | B. 2 | CH₂ | (morpholinyl) | (±); m.p. 284° C.; HCl (1:1) |

C. Pharmacological Example

EXAMPLE C.1

"mCPP Test on Rats"

Rats were treated with the test compound at a dose varying between 0.0025 mg/kg and 40 mg/kg body weight at a pre-test time T of 1 hour, and with 1 mg/kg mCPP (metachlorophenylpiperazine), injected intravenously, 15 minutes prior to the test. After pre-test time T elapsed, treated rats were submitted to the "Open Field Test on Rats" as described in Drug. Dev. Res. 18, 119–144 (1989), but using an infra-red light source instead of a Kleverlux® (12 V/20 W) light source. A dose at which 40% of the tested rats showed suppression of the mCPP induced effects, i.e. mCPP-antagonism, was defined as an active dose. Compounds number 1, 2, 4 and 9 were active at a test dose of 2.5 mg/kg or less.

EXAMPLE C.2

In Vitro Binding Affinity for $5HT_{2A}$ and $5\text{-}HT_{2C}$ Receptors

The interaction of the compounds of formula (I) with $5\text{-}HT_{2A}$ and $5\text{-}HT_{2C}$ receptors was assessed in in vitro radioligand binding experiments. In general, a low concentration of a radioligand with a high binding affinity for the receptor is incubated with a sample of a tissue preparation enriched in a particular receptor (1 to 5 mg tissue) in a buffered medium (0.2 to 5 ml). During the incubation, the radioligands bind to the receptor. When equilibrium of binding is reached, the receptor bound radioactivity is separated from the non-bound radioactivity, and the receptor bound activity is counted. The interaction of the test compounds with the receptors is assessed in competition binding experiments. Various concentrations of the test compound are added to the incubating mixture containing the tissue preparation and the radioligand. Binding of the radioligand will be inhibited by the test compound in proportion to its binding affinity and its concentration. The radioligand used for $5\text{-}HT_{2A}$ binding affinity is $^{3}H$-ketanserin and the tissue used is the frontal cortex of the rat. At a test concentration of $10^{-7}$ M, the compounds with number 3, 4, 5, 8 and 9 produced an inhibition of the $5\text{-}HT_{2A}$ receptor of more than 40%, and the other compounds produced an inhibition of less than 40%. The radioligand used for $5\text{-}HT_{2C}$ binding affinity is $^{3}H$-mesulergine and the tissue used is the choroid plexus of the pig. At a test concentration of $10^{-7}$ M, the compounds with number 1, 3, 4, 5, 6, 7, 8 and 9 produced an inhibition of the $5\text{-}HT_{2C}$ receptor of more than 40%, and compound number 2 produced an inhibition of less than 40%.

D. Composition Examples

"Active ingredient" (A.I.) as used throughout these examples relates to a compound of formula (I), a pharmaceutically acceptable acid addition salt, a stereochemically isomeric form thereof or a N-oxide form thereof.

EXAMPLE D.1

Oral Solution

Methyl 4-hydroxybenzoate (9 g) and propyl 4-hydroxybenzoate (1 g) were dissolved in boiling purified water (4 l). In 3 l of this solution were dissolved first 2,3-dihydroxybutanedioic acid (10 g) and thereafter A.I (20 g). The latter solution was combined with the remaining part of the former solution and 1,2,3-propanetriol (12 l) and sorbitol 70% solution (3 l) were added thereto. Sodium saccharin (40 g) were dissolved in water (500 ml) and raspberry (2 ml) and gooseberry essence (2 ml) were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE D.2

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinylpyrrolidone (10 g) in water (200 ml). The wet powder mixture was sieved, dried and sieved again. Then there was added microcrystalline cellulose (100 g) and hydrogenated vegetable oil (15 g). The whole was mixed well and compressed into tablets, giving 10,000 tablets, each containing 10 mg of the active ingredient.

Coating

To a solution of methyl cellulose (10 g) in denatured ethanol (75 ml) there was added a solution of ethyl cellulose (5 g) in dichloromethane (150 ml). Then there were added dichloromethane (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinylpyrrolidone (5 g) and concentrated colour suspension (30 ml) and the whole was homogenated. The tablet cores were coated with the thus obtained mixture in a coating apparatus.

EXAMPLE D.3

Injectable Solution

Methyl 4-hydroxybenzoate (1.8 g) and propyl 4-hydroxybenzoate (0.2 g) were dissolved in boiling water (500 ml) for injection. After cooling to about 50° C. there were added while stirring lactic acid (4 g), propylene glycol (0.05 g) and A.I. (4 g). The solution was cooled to room temperature and supplemented with water for injection q.s. ad 1000 ml, giving a solution comprising 4 mg/ml of A.I. The solution was sterilized by filtration and filled in sterile containers.

What is claimed is:

1. A compound of formula

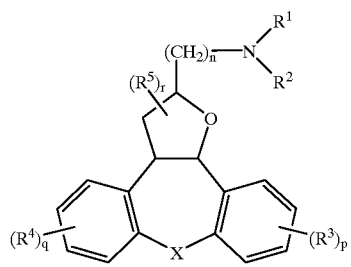

(I)

a N-oxide form, a pharmaceutically acceptable addition salt or a stereochemically isomeric form thereof, wherein:

n is zero, 1, 2, 3, 4, 5, or 6;
p is zero, 1, 2, 3 or 4;
q is zero, 1, 2, 3 or 4;
r is zero, 1, 2, 3, 4 or 5;
$R^1$ and $R^2$ each independently are hydrogen; $C_{1-6}$alkyl; $C_{1-6}$alkylcarbonyl; halomethylcarbonyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl; or $R^1$ and $R^2$ taken together with the nitrogen atom to which they are attached may form a morpholinyl ring or a radical of formula:

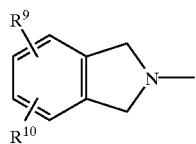
(a)

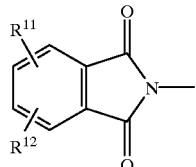
(b)

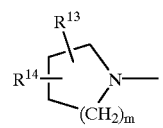
(c)

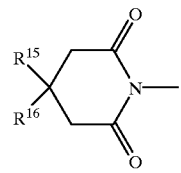
(d)

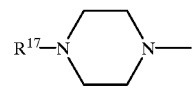
(e)

wherein:
$R^9$, $R^{10}$, $R^{11}$ and $R^{12}$ each independently are hydrogen, halo, halomethyl, or $C_{1-6}$alkyl;
m is zero, 1, 2, or 3;
$R^{13}$, $R^{14}$, $R^{15}$ and $R^{16}$ each independently are hydrogen, $C_{1-6}$alkyl, aryl or arylcarbonyl; or
$R^{15}$ and $R^{16}$ taken together may form a bivalent radical $C_{4-5}$alkanediyl;
$R^{17}$ is hydrogen; $C_{1-6}$alkyl; $C_{1-6}$alkylcarbonyl; halomethylcarbonyl;
$C_{1-6}$alkyloxycarbonyl; aryl; di(aryl)methyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl;
each $R^3$ independently is halo, cyano, hydroxy, halomethyl, halomethoxy, carboxyl, nitro, amino, mono- or di($C_{1-6}$alkyl)amino, $C_{1-6}$alkylcarbonylamino, aminosulfonyl, mono- or di($C_{1-6}$alkyl)aminosulfonyl, $C_{1-6}$alkyl, $C_{1-6}$alkyloxy, $C_{1-6}$alkylcarbonyl, $C_{1-6}$alkyloxycarbonyl;
each $R^4$ independently is halo, cyano, hydroxy, halomethyl, halomethoxy, carboxyl, nitro, amino, mono- or di($C_{1-6}$alkyl)amino, $C_{1-6}$alkylcarbonylamino, aminosulfonyl, mono- or di($C_{1-6}$alkyl)aminosulfonyl, $C_{1-6}$alkyl, $C_{1-6}$alkyloxy, $C_{1-6}$alkylcarbonyl, $C_{1-6}$alkyloxycarbonyl;
each $R^5$ independently is $C_{1-6}$alkyl, cyano or halomethyl;
X is $CR^6R^7$, $NR^8$, O, S, S(=O) or S(=O)$_2$; wherein
$R^6$ and $R^7$ each independently are hydrogen, hydroxy, $C_{1-6}$alkyl, halomethyl, $C_{1-6}$alkyloxy or $R^6$ and $R^7$ taken together may form methylene; mono- or di(cyano)methylene; a bivalent radical of formula —(CH$_2$)$_2$—, —(CH$_2$)$_3$—, —(CH$_2$)$_4$—, —(CH$_2$)$_5$—, —O—(CH$_2$)$_2$—O—, —O—(CH$_2$)$_3$—O—; or, together with the carbon atom to which they are attached, a carbonyl;

R$^8$ is hydrogen, C$_{1-6}$alkyl, C$_{1-6}$alkylcarbonyl, arylcarbonyl, arylC$_{1-6}$alkylcarbonyl, C$_{1-6}$alkylsulfonyl, arylsulfonyl or arylC$_{1-6}$alkylsulfonyl;

aryl is phenyl; or phenyl substituted with 1, 2, or 3 substituents selected from halo, hydroxy, C$_{1-6}$alkyl and halomethyl;

provided that the compound is other than (±)-3,3a,8,12b-tetrahydro-N-methyl-2H-dibenzo[3,4:6,7]-cyclohepta[1,2-b]furan-2-methanamine oxalic acid.

2. A compound as claimed in claim 1 wherein the compound is other than 3,3a,8,12b-tetrahydro-N-methyl-2H-dibenzo[3,4:6,7]-cyclohepta[1,2-b]furan-2-methanamine.

3. A compound as claimed in claim 1 wherein R$^{13}$, R$^{14}$, R$^{15}$ and R$^{16}$ each independently are hydrogen or C$_{1-6}$alkyl.

4. A compound as claimed in any one of claims 1 to 3 wherein X is CR$^6$R$^7$ or O.

5. A compound as claimed in claim 1 wherein R$^1$ and R$^2$ both are C$_{1-6}$alkyl or R$^1$ and R$^2$ are taken together with the nitrogen atom to which they are attached and form a morpholinyl ring; a radical of formula (c) or a radical of formula (e).

6. A compound as claimed in claim 1 wherein the substituents on carbon atoms 3a and 12b have the trans configuration.

7. A compound as claimed in claim 1 wherein r, p and q are zero.

8. A compound as claimed in claim 1 wherein p is 1 and R$^3$ is halo, C$_{1-6}$alkyl or C$_{1-6}$alkyloxy.

9. A compound as claimed in claim 1 wherein q is 1 and R$^4$ is halo, C$_{1-6}$alkyl or C$_{1-6}$alkyloxy.

10. A compound as claimed in claim 1 wherein the compounds is 3,3a,8,12b-tetrahydro-N,N-dimethyl-2H-dibenzo[3,4:6,7]cyclohepta[1,2-b]furan-2-methanamine; a stereochemically isomeric form or a pharmaceutically acceptable addition salt thereof, or an N-oxide form thereof.

11. A composition comprising a pharmaceutically acceptable carrier and, as active ingredient, a therapeutically effective amount of a compound as claimed in claim 1.

12. A process of preparing a compound as described in claim 1, characterized in that:
a) an intermediate of formula (II) is N-alkylated with an intermediate of formula (III)

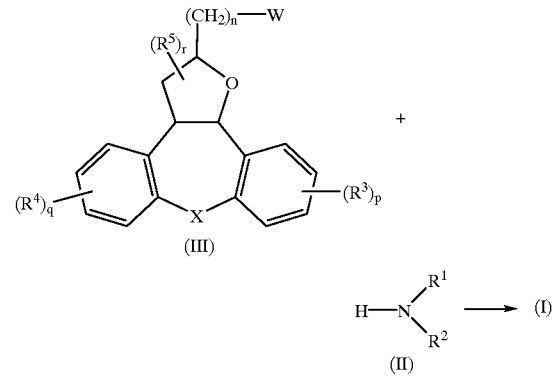

wherein in the intermediates (II) and (III) R$^1$ to R$^5$, n, p, q, r and X are defined as in claim 1 and W is a suitable leaving group; in a reaction-inert solvent and, optionally, in the presence of a suitable base;
b) converting compounds of formula (I) into each other following art-known transformations, and further, if desired, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms or N-oxide forms thereof.

\* \* \* \* \*